(12) United States Patent
Chen

(10) Patent No.: US 9,173,624 B2
(45) Date of Patent: Nov. 3, 2015

(54) SYSTEM AND METHOD FOR MULTI-ENERGY X-RAY IMAGING USING A POLYCHROMATIC SOURCE

(71) Applicant: Wisconsin Alumni Research Foundation, Madison, WI (US)

(72) Inventor: Guang-Hong Chen, Madison, WI (US)

(73) Assignee: WISCONSIN ALUMNI RESEARCH FOUNDATION, Madison, WI (US)

(*) Notice: Subject to any disclaimer, the term of this patent is extended or adjusted under 35 U.S.C. 154(b) by 190 days.

(21) Appl. No.: 14/053,211

(22) Filed: Oct. 14, 2013

(65) Prior Publication Data

US 2015/0103971 A1 Apr. 16, 2015

(51) Int. Cl.
*A61B 6/03* (2006.01)
*G01N 23/087* (2006.01)
*G06T 11/00* (2006.01)
*A61B 6/00* (2006.01)

(52) U.S. Cl.
CPC .............. *A61B 6/482* (2013.01); *G01N 23/087* (2013.01); *G06T 11/005* (2013.01); *A61B 6/032* (2013.01); *A61B 6/52* (2013.01); *A61B 6/5211* (2013.01); *A61B 6/5235* (2013.01); *A61B 6/5294* (2013.01)

(58) Field of Classification Search
CPC ............ A61B 6/02; A61B 6/03; A61B 6/032; A61B 6/482; A61B 6/52; A61B 6/5205; A61B 6/5229; A61B 6/5235; A61B 6/5294; G01N 23/00; G01N 23/06; G01N 23/08; G01N 23/083; G01N 23/087; H04N 5/32; H04N 5/335; G06T 5/00; G06T 5/40; G06T 5/50; G06T 7/0012; G06T 7/0014; G06T 7/0079; G06T 11/00; G06T 11/003; G06T 11/005; G06T 11/006; G06T 2207/10081; G06T 2207/10072; G06T 2207/20; G06T 2207/20021; G06T 2207/20112; G06T 2207/20148; G06T 2207/20212; G06T 2207/30; G06T 2210/00; G06T 2210/41; G06T 2211/00; G06T 2211/40; G06T 2211/408
USPC ............... 378/4, 5, 16, 62, 91, 162, 165, 204, 378/210, 901; 382/128, 131, 168, 171–174, 382/209, 217, 218, 220, 276, 325
See application file for complete search history.

(56) References Cited

U.S. PATENT DOCUMENTS

2006/0109949 A1* 5/2006 Tkaczyk et al. .................. 378/4

OTHER PUBLICATIONS

Gao, et al., Multi-energy CT Based on a Prior Rank, Intensity and Sparsity Model (PRISM), Inverse Probl., 2011, 27(11): doi:10.1088/0266-5611/27/11/115012.
Gonzales, et al., Full-Spectrum CT Reconstruction Using a Weighted Least Squares Algorithm With an Energy-Axis Penalty, IEEE Transactions on Medical Imaging, 2011, 30(2):173-183.
Hurrell, et al., Spectral Hounsfield Units: A New Radiological Concept, European Radiology, 2012, 22:1008-1013.

* cited by examiner

*Primary Examiner* — Anastasia Midkiff
(74) *Attorney, Agent, or Firm* — Quarles & Brady, LLP

(57) ABSTRACT

A system and method for generating multi-energy computed tomography images of a subject using a polychromatic x-ray source with single spectrum includes acquiring a measure of a polychromatic spectrum of a polychromatic x-ray beam generated by the polychromatic x-ray source. The method also includes acquiring attenuation data generated by operating the polychromatic x-ray source, segmenting the attenuation data based on a plurality of component criteria to create plurality of segmented datasets, and generating template data from the segmented datasets. Using the template data and the measure of the polychromatic spectrum, polychromatic synthetic data is generated. Using the template data and each of the segmented datasets, component synthetic data is generated. Using the attenuation data, the polychromatic synthetic data, and the component synthetic data, a plurality of multi-energy images, including separable images weighted for each of the component criteria, is reconstructed.

20 Claims, 3 Drawing Sheets

SYSTEM AND METHOD FOR MULTI-ENERGY X-RAY IMAGING USING A POLYCHROMATIC SOURCE

STATEMENT REGARDING FEDERALLY SPONSORED RESEARCH

This invention was made with government support under EB009699 and CA169331 awarded by the National Institutes of Health. The government has certain rights in the invention.

CROSS-REFERENCE TO RELATED APPLICATIONS

N/A

BACKGROUND OF THE INVENTION

The field of the invention is systems and methods for creating images using an ionizing radiation source. More particularly, the invention relates to systems and methods for creating medical images using a polychromatic source with single energy spectrum to create multi-energy imaging data sets and corresponding images.

Dual-energy computed tomography (CT) imaging was proposed in 1970s and, since then, has experienced several up-and-downs in practical implementation and also applications. In recent five years, dual-energy CT has been commercialized by several companies to provide quantitative discrimination in materials such as iodine and calcium and focused on clinical applications, such as the differentiations between different kinds of renal stones. While the practical uses of dual-energy CT imaging has been established, there are a variety of lingering challenges that have impeded the wide-spread adoption of dual-energy CT imaging in clinics.

First, the commercially-available dual-energy CT systems require specialized hardware, such as data acquisition systems. For example, turning to FIGS. 1 and 2, a traditional dual-energy, CT system is illustrated, such as is commercially available. In particular, a dual-energy CT imaging system 10 includes a gantry 12 having a one or more x-ray sources 13 (13') that project a fan beam or cone beam of x-rays 14 (14') toward a detector array 16 (16') on the opposite side of the gantry 12. As illustrated, there may be a single source 13 or two or more source 13'. That is, some commercially-available, dual-energy systems employ a single source 13 that is switched between high and low energies and other commercially-available, dual-energy systems employ two dedicated sources 13, 13' that are used to generate the high and low energies. That is, to enable dual-energy CT imaging, one either require two tube two detector technique, or one has to have special x-ray generator, tube, and also detector to enable fast kV switching acquisition technique, or a special sandwich detector or photon counting detector to enable energy resolving x-ray detections. The detector array 16 (16') is formed by a number of detector elements 18 that together sense the projected x-rays that pass through a medical patient 15. Each detector element 18 (18') produces an electrical signal in response to receiving photon or bunches of photons.

During a scan to acquire x-ray projection data, the gantry 12 and the components mounted thereon rotate about a center of rotation 19 located within the patient 15 to acquire attenuation data. The rotation of the gantry and the operation of the x-ray source(s) 13 (13') are governed by a control mechanism 20 of the CT system. The control mechanism 20 includes an x-ray controller 22 that provides power and timing signals to the x-ray source(s) 13 (13') and a gantry motor controller 23 that controls the rotational speed and position of the gantry 12. A data acquisition system (DAS) 24 in the control mechanism 20 samples analog data from detector elements 18 and converts the data to digital signals for subsequent processing. An image reconstructor 25, receives sampled and digitized x-ray data from the DAS 24 and performs high speed image reconstruction. The reconstructed image is applied as an input to a computer 26 which stores the image in a mass storage device 28.

The computer 26 also receives commands and scanning parameters from an operator via a console 30 that has a keyboard. An associated display 32 allows the operator to observe the reconstructed image and other data from the computer 26. The operator supplied commands and parameters are used by the computer 26 to provide control signals and information to the DAS 24, the x-ray controller 22, and the gantry motor controller 23. In addition, the computer 26 operates a table motor controller 34 that controls a motorized table 36 to position the patient 15 in the gantry 12.

Whether employing two, dedicated sources 13, 13' or switching operation of a single source 13 between two tube potentials, these dual- or multi-energy imaging systems are generally of higher cost and complexity than traditional imaging systems due to the need for specialized hardware and software, such as additional sources 13', detector arrays 16', and communications and software for processing feedback from different energy levels from individual detector elements 18, 18'.

Second, regardless of the hardware, maintenance, and operational cost and complexities, traditional dual- or multi-energy CT imaging systems subject the patient 15 to a higher dose of ionizing radiation than a non-dual-energy CT imaging process. That is, a dose of high-energy radiation is delivered to the patient 15 and a does of low-energy radiation is delivered to the patient 15.

Therefore, it would be desirable to provide systems and methods for performing dual- or multi-energy imaging without the need for two separable x-ray energy spectra and also highly-specialized, expensive, and complex hardware and/or delivering two doses of radiation tot the patient.

SUMMARY OF THE INVENTION

The present invention overcomes the aforementioned drawbacks by providing a system and method for generating multi-energy tomographic images using a single-energy spectrum imaging system. The present invention provides a system and method for uncovering energy information available when a single polychromatic x-ray spectrum generated from a single-energy x-ray source is used to, thereby, derive multi-energy, such as dual-energy, images when using a traditional, single-energy spectrum imaging system with a polychromatic source.

In accordance with one aspect of the invention, a system for generating multi-energy computed tomography (CT) images of a subject is disclosed. The system includes a polychromatic x-ray source configured to generate a polychromatic x-ray beam and a detector array arranged to receive the polychromatic x-ray beam after traversing through the subject and generate attenuation data responsive to receiving the polychromatic x-ray beam. The system also includes a computer system configured to acquire a measure of an x-ray spectrum of the polychromatic x-ray beam, receive the attenuation data from the detector array, and segment the attenuation data based on a plurality of component criteria to create plurality of segmented datasets. The computer system is further configured to generate template data from the segmented datasets and, using the template data and the measure of the x-ray spectrum, generate polychromatic synthetic data. The computer system, using the template data and each of the segmented datasets, generates component synthetic data. Also, using the attenuation data, the polychromatic synthetic data, and the component synthetic data, the computer system reconstructs a plurality of multi-energy images, including separable images weighted for each of the component criteria.

In accordance with another aspect of the invention, a method is disclosed for generating multi-energy computed tomography images of a subject using a polychromatic x-ray source with a single energy spectrum. The method includes acquiring a measure of a spectrum of a polychromatic x-ray beam generated by the polychromatic x-ray source, acquiring attenuation data generated by operating the single spectrum polychromatic x-ray source, and segmenting the attenuation data based on a plurality of attenuation thresholds corresponding to selected constituent materials of the subject to create plurality of segmented datasets. The method also includes generating template data from the plurality of segmented datasets by replacing portions of the attenuation data with a mean CT number of the selected constituent materials, generating polychromatic synthetic data by forward projecting the template data using the attenuation data, and generating component synthetic data by forward projecting the template data using the plurality of segmented datasets. The method further includes using the attenuation data, the polychromatic synthetic data, and the component synthetic data, reconstruct a plurality of multi-energy images, including separable images weighted for each selected constituent materials.

In accordance with yet another aspect of the invention, a method is disclosed for generating multi-energy computed tomography images of a subject using a polychromatic x-ray source with a single energy spectrum. The method includes acquiring a measure of a spectrum of a polychromatic x-ray beam generated by the single polychromatic x-ray source, acquiring attenuation data generated by operating the single polychromatic x-ray source, and segmenting the attenuation data based on a plurality of component criteria to create plurality of segmented datasets. The method also includes generating template data from the segmented datasets and, using the template data and the measure of the spectrum, generating polychromatic synthetic data. The method further includes generating component synthetic data using the template data and each of the segmented datasets. Using the attenuation data, the polychromatic synthetic data, and the component synthetic data, a plurality of multi-energy images are reconstructed that include separable images weighted for at least one of the component criteria.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
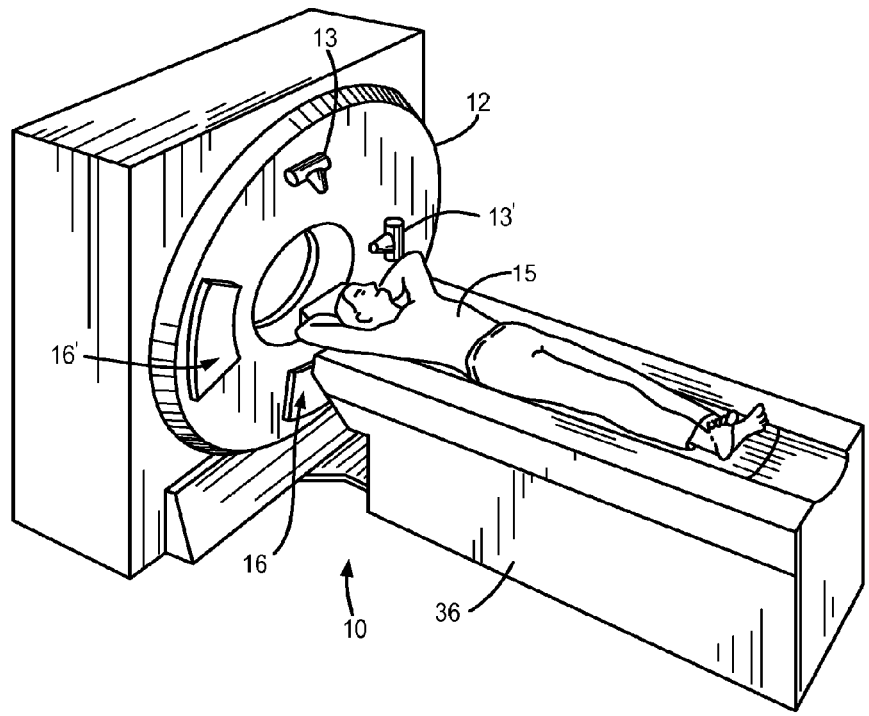
FIG. 1 is a perspective view of a traditional, dual-energy, x-ray, computed tomography (CT) system.
Figure 2:
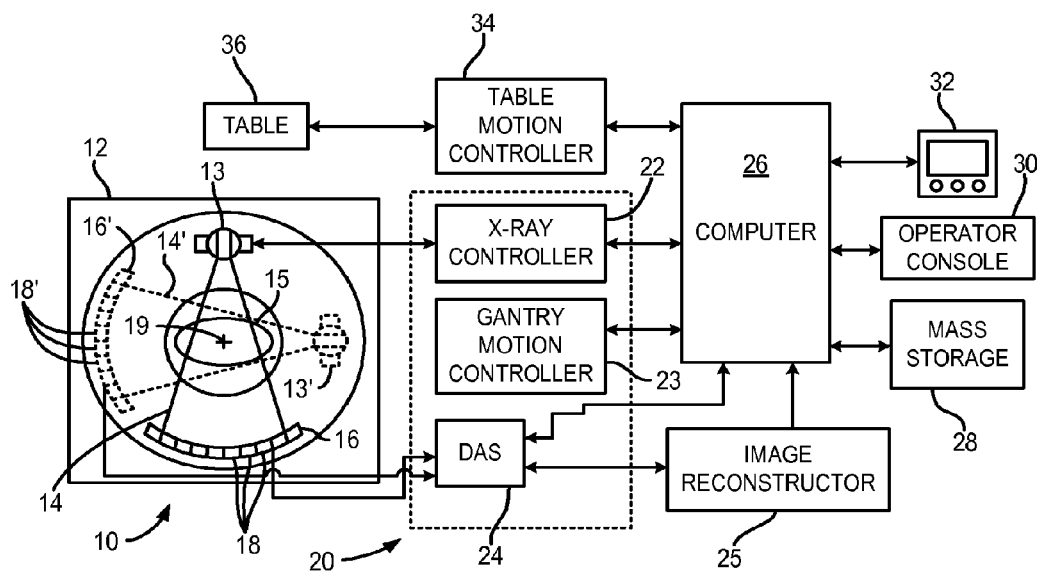
FIG. 2 is a block diagram of the traditional, dual-energy, x-ray, CT system of FIG. 1.
Figure 3:
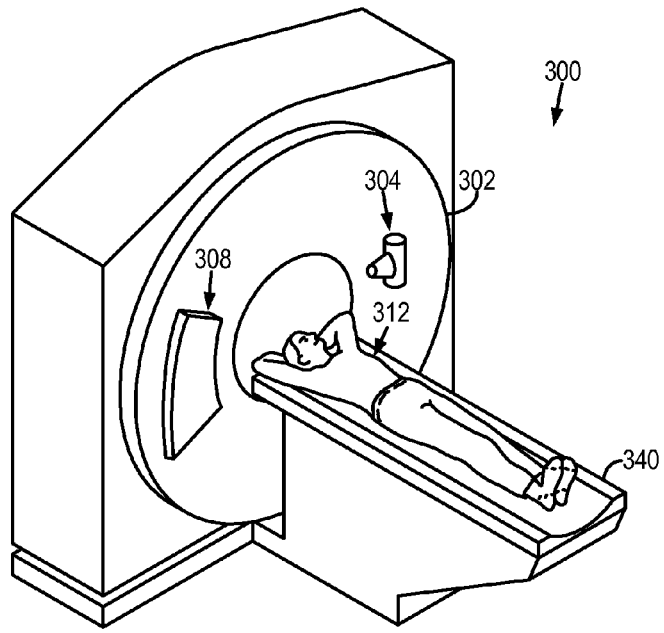
FIG. 3 a perspective view of a polychromatic, x-ray, CT system configured for use with the present invention.
Figure 4:
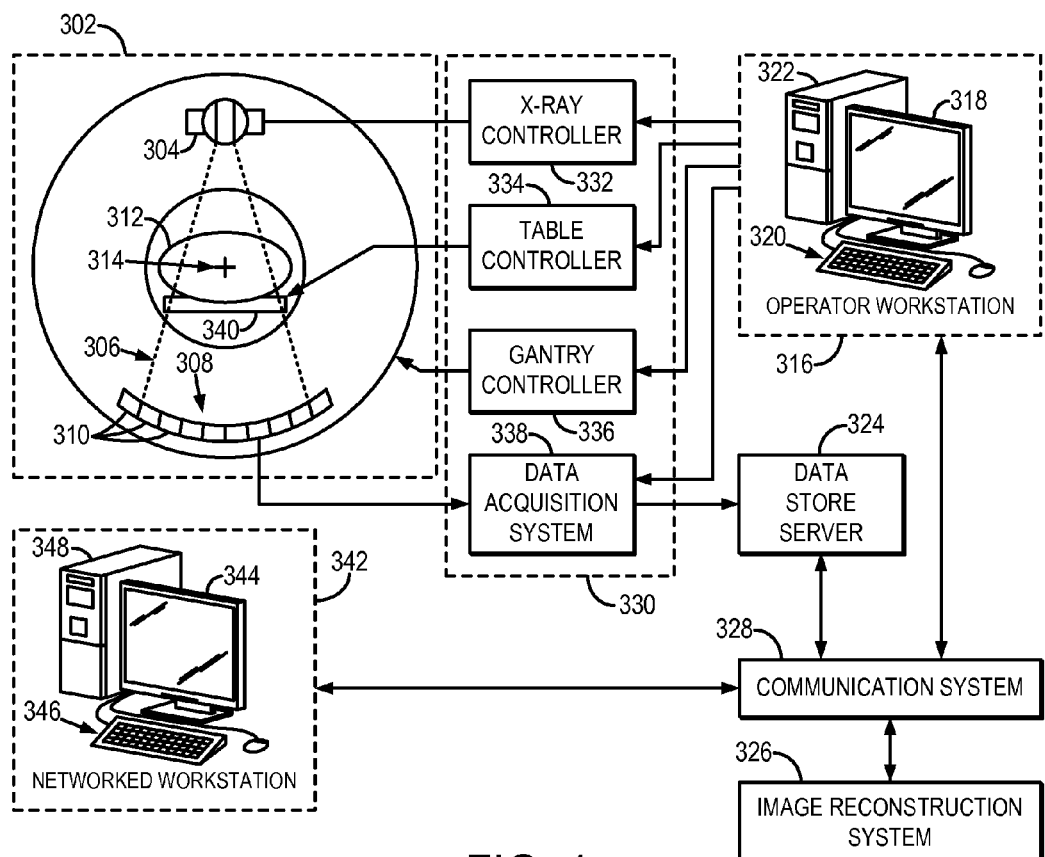
FIG. 4 is a block diagram of the polychromatic, x-ray, CT system of FIG. 3.

Referring particularly now to FIGS. 3 and 4, an example of an x-ray computed tomography ("CT") imaging system 300 is illustrated. The CT system includes 300 a gantry 302, to which one, polychromatic, x-ray source 304 is coupled. As will be explained, energy information associated with using a polychromatic x-ray source with single spectrum is traditionally viewed as undesirable because the polychromatic-nature of the x-ray source is contrary to the objective of single-energy imaging. However, the present invention unlocks and utilizes such information that was traditionally not available to, thereby, provide multi-energy imaging information without the cost or complexity of traditional multi-energy systems or the added patient dose required by such traditional, multi-energy systems.

The x-ray source 304 projects a polychromatic x-ray beam 306, which may be a fan-beam or cone-beam of x-rays, towards a detector array 308 on the opposite side of the gantry 302. The detector array 308 includes a number of x-ray detector elements 310. Together, the x-ray detector elements 310 sense the projected x-rays 306 that pass through a subject 312, such as a medical patient or an object undergoing examination, that is positioned in the CT system 300. Each x-ray detector element 310 produces an electrical signal in response to an impinging polychromatic x-ray beam and, hence, the attenuation of the beam as it passes through the subject 312. In some configurations, each x-ray detector 310 may be capable of counting the number of x-ray photons that impinge upon the detector 310. During a scan to acquire x-ray projection data, the gantry 302 and the components mounted thereon rotate about a center of rotation 314 located within the CT system 300.

The CT system 300 also includes an operator workstation 316, which typically includes a display 318; one or more input devices 320, such as a keyboard and mouse; and a computer processor 322. The computer processor 322 may include a commercially available programmable machine running a commercially available operating system. The operator workstation 316 provides the operator interface that enables scanning control parameters to be entered into the CT system 300. In general, the operator workstation 316 is in communication with a data store server 324 and an image reconstruction system 326. By way of example, the operator workstation 316, data store sever 324, and image reconstruction system 326 may be connected via a communication system 328, which may include any suitable network connection, whether wired, wireless, or a combination of both. As an example, the communication system 328 may include both proprietary or dedicated networks, as well as open networks, such as the internet.

The operator workstation 316 is also in communication with a control system 330 that controls operation of the CT system 300. The control system 330 generally includes an x-ray controller 332, a table controller 334, a gantry controller 336, and a data acquisition system 338. The x-ray controller 332 provides power and timing signals to the x-ray source 304 and the gantry controller 336 controls the rotational speed and position of the gantry 302. The table controller 334 controls a table 340 to position the subject 312 in the gantry 302 of the CT system 300.

The DAS 338 samples data from the detector elements 310 and converts the data to digital signals for subsequent processing. For instance, digitized x-ray data is communicated from the DAS 338 to the data store server 324. The image reconstruction system 326 then retrieves the x-ray data from the data store server 324 and reconstructs an image therefrom. The image reconstruction system 326 may include a commercially available computer processor, or may be a highly parallel computer architecture, such as a system that includes multiple-core processors and massively parallel, high-density computing devices. Optionally, image reconstruction can also be performed on the processor 322 in the operator workstation 316. Reconstructed images can then be communicated back to the data store server 324 for storage or to the operator workstation 316 to be displayed to the operator or clinician.

The CT system 300 may also include one or more networked workstations 342. By way of example, a networked workstation 342 may include a display 344; one or more input devices 346, such as a keyboard and mouse; and a processor 348. The networked workstation 342 may be located within the same facility as the operator workstation 316, or in a different facility, such as a different healthcare institution or clinic.

The networked workstation 342, whether within the same facility or in a different facility as the operator workstation 316, may gain remote access to the data store server 324 and/or the image reconstruction system 326 via the communication system 328. Accordingly, multiple networked workstations 342 may have access to the data store server 324 and/or image reconstruction system 326. In this manner, x-ray data, reconstructed images, or other data may exchanged between the data store server 324, the image reconstruction system 326, and the networked workstations 342, such that the data or images may be remotely processed by a networked workstation 342. This data may be exchanged in any suitable format, such as in accordance with the transmission control protocol ("TCP"), the internet protocol ("IP"), or other known or suitable protocols.

Figure 5:
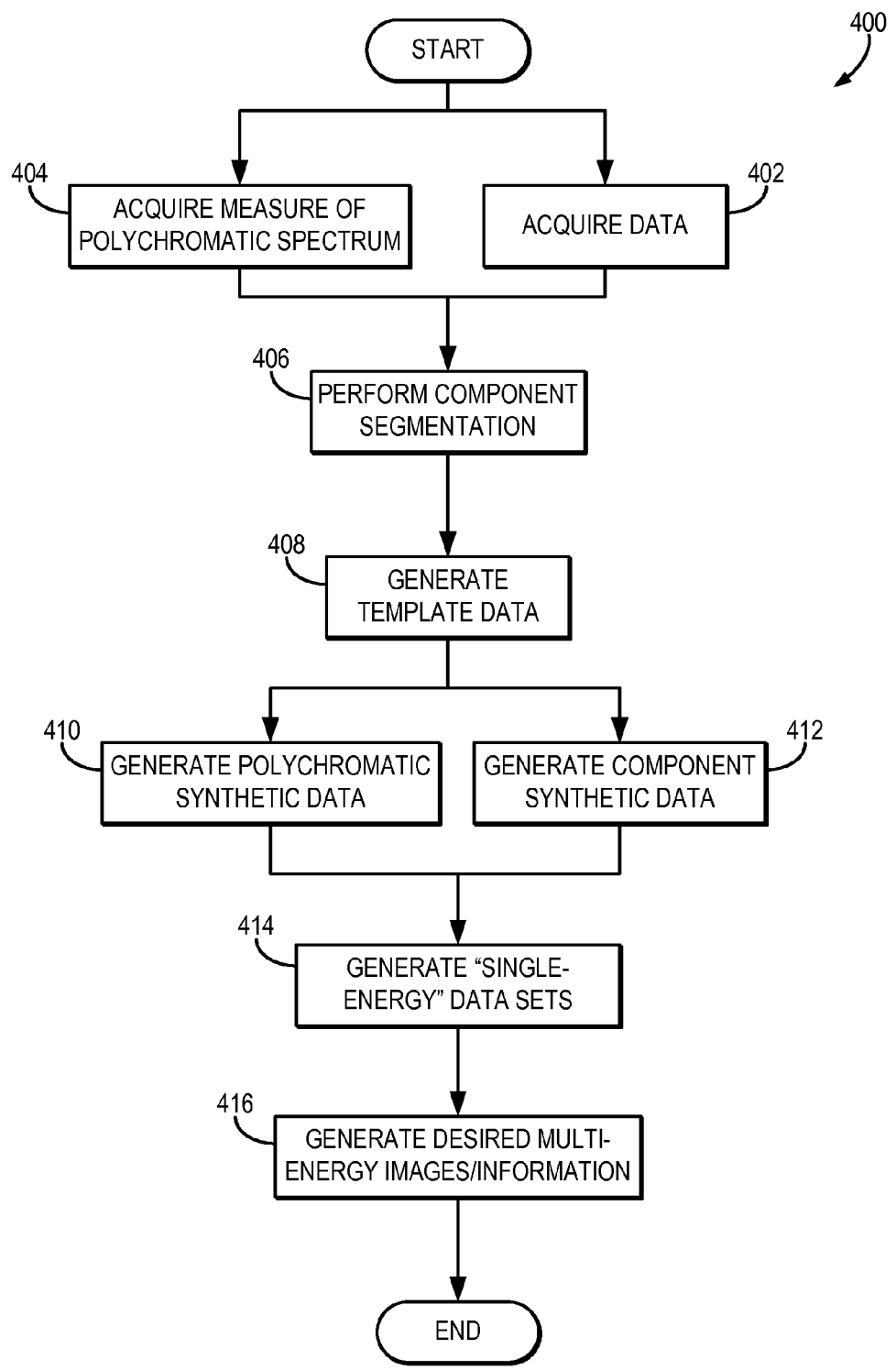
FIG. 5 is a flow chart setting forth steps of an example of a method in accordance with the present invention.

Referring particularly now to FIG. 5, the steps of a process 400 for performing multi-energy, such as dual-energy, CT imaging is illustrated. At process block 402, polychromatic CT data is acquired. This step 402 may be performed using any currently available CT systems capable of delivering a polychromatic x-ray beam and acquiring and processing the data using that polychromatic x-ray beam in a manner, such as described below. Thus, as will be described, the present process allows clinical access to multi-energy, including dual-energy, CT imaging without the need for a second x-ray source or specialized hardware and software to enable a single source to rapidly switch between high and low energy levels. Rather, the present process leverages available multi-energy information that is acquired using current data acquisition systems with a polychromatic x-ray source. Therefore, as will be described, multi-energy image information can be derived with the need to subject a patient to an elevated radiation dose over a standard CT imaging process, such as is required in traditional dual-energy CT imaging processes. Rather, as will be described, the present invention provides a system and method to derive quantitative dual-energy CT as product of a traditional, single-energy CT acquisition using a polychromatic source.

After the data is acquired at process block 402, the multi-energy information, when acquired by a traditional acquisition system, is not readily apparent. Rather, the present invention provides a way to separate the acquired multi-energy information into difference energy levels, even when using an energy-integrating detector system to allow images to be reconstructed, including high and low energy level images, and generate dual-energy CT images with desirable noise property. To allow multi-energy, including dual-energy, CT images to be generated from the single-energy data acquisitions, at process block 404, a measure of polychromatic x-ray spectrum is acquired. As illustrated, process block 402 and 404 may be performed in parallel or may be performed in any serial order. Acquiring a measure of the polychromatic spectrum may be achieved in a variety of ways. For example, a measuring process may be performed in conjunction, such as before or after, the acquisition of data at process block 402. Alternatively, a measure of the polychromatic spectrum may be stored and accessed or referenced as needed. That is, this measure of polychromicity, i.e., spectrum, may be an a priori measurement stored on a non-transitory, computer-readable storage medium and accessed by a computer system carrying out the process described with respect to FIG. 5 by carrying out computer instructions stored on a non-transitory, computer-readable storage medium.

With the acquired data and a measure of the polychromatic spectrum in hand, a multi-component image segmentation is performed at process block 406. For example, a multi-component image segmentation may be performed on CT images reconstructed from data acquired at process block 402. Alternatively, segmentation may be performed on raw/non-reconstructed data acquired at process block 402. Whether in the image domain or simply attenuation data, segmentation may be performed, for example, using a thresholding. The segmentation may use, for example, three-components, such as bone, soft tissue, and air. Due to the dramatic difference in CT number for these three examples, the thresholding segmentation may be automated and performed in either domain.

At process block 408, template data or a template image is generated from the segmented data. For example, the component segmentation at process block 406 allows the image data to be replaced by the mean CT number of the three segmented components to generate a template image at process block. At process block 410, the template image is then forward projected using the measured real x-ray spectrum to generate polychromatic synthetic projection data. At process block 412, the template image is also forward projected using the attenuation coefficients of the three components at any given energies.

At process block 414, an effective "single-energy" CT projection data is then generated by multiplying the original polychromatic x-ray projection data with a ratio of the projection data of a single component of the component synthetic data and polychromatic synthetic data. This step recalibrates the original polychromatic projection data into the effective single-energy projection data at any given energy level. For example, if a "dual-energy" image dataset is desired, a single-energy, "high-energy" dataset and a single-energy, "low-energy" dataset may be generated at process block 414. In this example, after the generation of a high- and low-effective single-energy projection datasets, traditional dual-energy CT data processing can be applied to generate the desired dual-energy information, such as material decomposition images and the like. To reduce the potential noise elevation in multi-energy processing, additional processing, such as a prior-image constrained compressed sensing (PICCS) noise reduction method, such as described in co-pending U.S. application Ser. Nos. 12/986,847 and 14/036,599, which are incorporated herein by reference in their entirety, can be applied to suppress noise for signal-to-noise ratio (SNR) enhancement.

This invention is applicable to any x-ray tomography data acquisition systems including diagnostic multi-slice CT scanners, C-arm CT scanners, on-board cone-beam CT scanners for radiation therapy, cone-beam CT scanners, and also the security CT scanners at the security checkpoints.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for generating multi-energy computed tomography (CT) images of a subject, the system comprising:
    a polychromatic x-ray source configured to generate a polychromatic x-ray beam;
    a detector array arranged to receive the polychromatic x-ray beam after traversing through the subject and generate attenuation data responsive to receiving the polychromatic x-ray beam;
    a computer system configured to:
        acquire a measure of a polychromatic spectrum of the polychromatic x-ray beam;
        receive the attenuation data from the detector array;
        segment the attenuation data based on a plurality of component criteria to create a plurality of segmented datasets;
        generate template data from the segmented datasets;
        using the template data and the measure of the polychromatic spectrum, generate polychromatic synthetic data;
        using the template data and each of the segmented datasets, generate component synthetic data; and
        using the attenuation data, the polychromatic synthetic data, and the component synthetic data, reconstruct a plurality of multi-energy images, including separable images weighted for each of the component criteria.

2. The system of claim 1 wherein the computer system is configured to generate polychromatic synthetic projection data by forward projecting the template data using the attenuation data.

3. The system of claim 1 wherein the computer is further configured to generate the component synthetic data by forward projecting the template data using the plurality of segmented datasets.

4. The system of claim 1 wherein the computer is further configured to reconstruct the plurality of multi-energy images by multiplying the attenuation data by a ratio of one of the plurality of segmented datasets and the polychromatic synthetic data to create one of the separable images weighted for each of the component criteria.

5. The system of claim 1 wherein the computer is further configured to select component criteria corresponding to attenuation thresholds of at least one of air, bone, and soft tissue.

6. The system of claim 1 wherein the polychromatic x-ray source is the only x-ray source.

7. The system of claim 1 wherein the computer is configured to control the polychromatic x-ray source to generate a polychromatic x-ray beam at a single, target energy.

8. The system of claim 1 wherein the computer is configured to acquire the measure of the polychromatic spectrum by accessing an a priori measurement stored on a non-transitory, computer-readable storage medium.

9. The system of claim 1 wherein the computer is configured to generate the template data by selecting a mean CT number associated with the component criteria.

10. A method for generating multi-energy computed tomography images of a subject using a polychromatic x-ray source with single spectrum, the method comprising:
    acquiring a measure of a polychromatic spectrum of a polychromatic x-ray beam generated by the polychromatic x-ray source with a single spectrum;
    acquiring attenuation data generated by operating the polychromatic x-ray source with a single spectrum;
    segmenting the attenuation data based on a plurality of attenuation thresholds corresponding to selected constituent materials of the subject to create a plurality of segmented datasets;
    generating template data from the plurality of segmented datasets by replacing portions of the attenuation data with a mean CT number of the selected constituent materials;
    generating polychromatic synthetic data by forward projecting the template data using the attenuation data;
    generating component synthetic data by forward projecting the template data using the plurality of segmented datasets; and
    using the attenuation data, the polychromatic synthetic data, and the component synthetic data, reconstruct a plurality of multi-energy images, including separable images weighted for each selected constituent materials.

11. The method of claim 10 wherein reconstructing includes multiplying the attenuation data by a ratio of a first of the plurality of segmented datasets and the polychromatic synthetic data to create one of the separable images weighted the first of the selected constituent materials.

12. The method of claim 10 wherein the selected constituent materials include bone, soft tissue, and air.

13. The method of claim 12 wherein the thresholds correspond to attenuations known to be associated with bone, soft tissue, and air.

14. The method of claim 10 wherein the polychromatic x-ray beam is generated using a single, target spectrum.

15. A method for generating multi-energy computed tomography images of a subject using a polychromatic x-ray source with single x-ray spectrum, the method comprising:
    acquiring a measure of a polychromatic spectrum of a polychromatic x-ray beam generated by the polychromatic x-ray source;
    acquiring attenuation data generated by operating the polychromatic x-ray source;
    segmenting the attenuation data based on a plurality of component criteria to create a plurality of segmented datasets;
    generating template data from the segmented datasets;
    using the template data and the measure of the polychromatic spectrum, generating polychromatic synthetic data;
    using the template data and each of the segmented datasets, generating component synthetic data; and
    using the attenuation data, the polychromatic synthetic data, and the component synthetic data, reconstructing a plurality of multi-energy images, including separable images weighted for at least one of the component criteria.

16. The method of claim 15 wherein generating polychromatic synthetic projection data is performed by forward projecting the template data using the attenuation data.

17. The method of claim 15 wherein generating the component synthetic data is performed by forward projecting the template data using the plurality of segmented datasets.

18. The method of claim 15 wherein reconstructing the plurality of multi-energy images is performed by multiplying the attenuation data by a ratio of one of the plurality of segmented datasets and the polychromatic synthetic data to create one of the separable images weighted for each of the component criteria.

19. The method of claim 15 further comprising selecting component criteria corresponding to attenuation thresholds of at least one of air, bone, and soft tissue.

20. The method of claim 15 further comprising controlling the polychromatic x-ray source to generate a single polychromatic x-ray beam at a single, target energy to acquire all of the attenuation data.

* * * * *